United States Patent [19]

Schossow

[11] Patent Number: 4,551,473

[45] Date of Patent: Nov. 5, 1985

[54] METHOD OF INHIBITING SNORING AND OBSTRUCTIVE SLEEP APNEA

[76] Inventor: George W. Schossow, 2316 Lilac La., White Bear Lake, Minn. 55110

[21] Appl. No.: 603,967

[22] Filed: Apr. 26, 1984

[51] Int. Cl.⁴ .................... A61K 31/44; A61K 31/135; A61K 31/195

[52] U.S. Cl. .................................... 514/305; 514/561; 514/648

[58] Field of Search ................ 424/330; 514/305, 561, 514/648

[56] References Cited

U.S. PATENT DOCUMENTS 2,991,225  7/1961  Harms .................................. 167/65

OTHER PUBLICATIONS

Goth, *Medical Pharmacology*, 1981, pp. 171 et seq.

Goodman and Gilman's, *The Pharmacological Basis of Therapeutics*, Sixth Edition, pp. 488 et seq.

J. B. Lippincott Company's, *Facts and Comparisons*, (A Loose-Leaf Drug Information Service, pp. 285-289a).

Edwin Kiester, Jr., 50 Plus, *A Little Night Music*, Feb. 1984, pp. 68-69.

Cardiovascular News, *Surgery Foils Obstructive Sleep Apnea*, Mar. 1984.

David N. F. Fairbanks, MD, Hospital Medicine, *Snoring: Not Funny—Not Hopeless*, Mar. 1984, pp. 173-184.

*Primary Examiner*—Stanley J. Friedman
*Attorney, Agent, or Firm*—Richard E. Brink

[57] ABSTRACT

Snoring and obstructive sleep apnea are relieved in most instances by administering an effective dose of a muscle relaxant that acts at the spinal or supra-spinal level. A presently preferred drug is orphenadrine citrate.

3 Claims, No Drawings

METHOD OF INHIBITING SNORING AND OBSTRUCTIVE SLEEP APNEA

BACKGROUND OF THE INVENTION

This invention relates to the inhibition or prevention of snoring and the obstructive sleep apnea that often accompanies snoring.

One of the most misunderstood ailments of human beings is the noisy breathing pattern that occurs in some persons during sleep. Afflicted persons may create so much sonic disturbance that they prevent sleep in bed partners, roommates, and sometimes persons several rooms distant. Throughout recorded history, snorers have been ridiculed, harassed, and subjected to the mounting hostility of other household members. As might be expected, an almost endless variety of well-meaning or defensive attempts have been made to control snoring; see, e.g., the more than 300 devices that have received U.S. patents for the control of snoring. Most such devices function by subjecting the unfortunate subject to unpleasant mechanical or electrical stimuli as soon as snoring commences and are successful only to the degree that the snorer is kept from sleeping.

As has been pointed out in such recent papers as that of David N. F. Fairbanks, M.D. ("Snoring: Not Funny—Not Hopeless", *Hospital Medicine*, March, 1984), the noise of snoring comes from vibrations of soft tissues in the collapsible part of the upper airway, involving the soft palate, uvula, tonsils and tonsillar pillars, base of the tongue, and pharyngeal muscles and mucosa. The most recent medical literature expresses the opinion that, for most persons, snoring is caused by the muscle relaxation that occurs during sleep. It is postulated that, as the muscles of the mouth, nose, and throat relax, the negative pressure that occurs during inspiration encourages the tongue to fall backward into the airway and vibrate against a relaxed and floppy soft palate and uvula. At the same time, the lateral pharyngeal structures are drawn inward, further constricting the airway and increasing the speed of air flow past the vibrating structures. Obesity, which further constricts the airway, increases the work of breathing and compounds the problem. Temporary swelling caused by hay fever, inflamed sinuses, etc., also narrow the air passages and may bring on snoring in a person normally free from that affliction; however, the use of antihistamines promotes drying of the mucous membranes and further promotes vibration of the relaxed structures. Smoking, two byproducts of which are carbon monoxide and formaldehyde, tends to dry or irritate the air passages, induce hypoxemia, and even put the swallowing muscles into spasm, tending to stimulate snoring. When an afflicted person uses central nervous system depressants such as alcoholic beverages or tranquilizers before retiring, it has been found that the tendency to snore is exacerbated.

Socially unattractive as snoring may be, the frequently accompanying sleep apnea is actually dangerous. In some cases, the relaxed tissues of the airway may so effectively seal off the passage to the lungs as to completely prevent inspiration. Persons suffering from this problem may actually stop breathing 30 to 300 times per night for periods of ten seconds to two minutes (three minutes may be fatal), consequently spending as much as half their sleep time with abnormally low blood oxygen levels. Such persons resume normal breathing, albeit briefly, when they wake into a lighter sleep stage, causing the relaxed muscles to tense sufficiently to relieve the obstruction. As will be appreciated, persons with obstructive sleep apnea spend an insufficient portion of their nighttime hours in the deep sleep stages that are essential for good rest, awakening unrefreshed and feeling sleepy much of the day. Cardiac arrhythmias may occur during apneic episodes, possibly leading to death in sleep in some instances.

In recent years, the most widely heralded way of curing the related problems of snoring and obstructive sleep apnea has been the surgical removal of what has been considered excess tissue in the air passageway by means of a palatopharyngoplasty, an operation that has been characterized as a "facelift of the throat." Although effective in many instances, the operation is painful, expensive, and fraught with the dangers accompanying any operation in the blood-rich throat area. Prior to the present invention, it is believed, there has never been a simple, safe, and inexpensive way to control snoring.

The present invention provides a simple, safe, and inexpensive way of medically curing snoring in the majority of cases. No invasive surgery is required, and the snorer is not subjected to the discomfort of electrical, mechanical, or psychological treatments.

In accordance with the invention, the snorer is treated by administering a conventional amount of certain muscle relaxants. In view of the fact that snoring is almost universally believed to be caused by relaxed muscles, such a treatment would seem to be clearly contraindicated. Surprisingly, however, it has been found that the expected worsening does not occur. In attempting to understand why the treatment is effective, the inventor has concluded that the conventionally accepted muscle relaxation theory of snoring has provided an incomplete explanation of what actually takes place. The inventor now hypothesizes that the cause of snoring is closely related to the balanced muscular structure of the human body, where every muscle or group of muscles is opposed by another muscle or group of muscles; such opposing muscles are known as "agonists" and "antagonists." In every such situation, the agonist tends to be stronger than the antagonist, or vice versa, depending on which of the two is normally exercised more. Muscles that work more strenuously tend to grow larger (hypertrophy) and become significantly stronger than those that work less. Since muscles perform their physiological function by contracting, the stronger muscle contracts more than the weaker during normal relaxation, in effect going into mild spasm. When a muscle relaxant is administered, however, the stronger muscle is relaxed to a state more nearly approximating that of the weaker muscle, tending to restore the normal balance, returning the structures on which they act to a neutral resting position.

Applying the discussion of the preceding paragraph to the problem of snoring, it is noted that the muscles involved are those used normally in swallowing. As one swallows, the soft palate is pulled back against the nasopharynx by the uppermost fibers of the superior pharyngeal constrictor. The levator palatini and the tensor palatini elevate the soft palate against the roof of the nasopharynx. The tongue, a bolus of food, or a volume of liquid pushing backward and upward also forces the soft palate backward and upward against the nasopharynx, thus sealing it off from the throat and preventing food or liquids from "going up the nose" during swallowing. Other pharyngeal constrictor muscles narrow the throat, forcing the food or liquid down the esophagus. Each of the muscles just discussed is opposed by other muscles, which do not ordinarily receive much exercise. Thus, for example, the muscles that move the soft palate downward and forward to open the nasopharynx to the oropharynx do not ordinarily do much work, except, perhaps during singing or yawning. Similarly, the genioglossus (the muscle that holds the tongue forward) is notoriously weak, receiving exercise essentially only during the socially unacceptable practice of "sticking out the tongue." During the relaxation accompanying sleep, the stronger swallowing muscles relax less than the weaker opposing muscles, encouraging the soft palate to move backward and upward, pulling the tongue backward, and constricting the throat. As a result, the entire airway is narrowed, the inspired air moves faster, and the relaxed tissues tend to vibrate; i.e., snoring occurs. If the nasopharynx becomes completely sealed off, air is inhaled through the mouth, and the narrowed oropharynx leads to a secondary form of snoring.

Administering a muscle relaxant tends to restore balance to the nasopharynx and oropharynx. No longer do the stronger muscles overpower the weaker ones. The tendency of the soft palate to move upward and backward is canceled out, the tendency of the tongue to fall back in the throat is counteracted, and constriction of the throat muscles is minimized. As a result, breathing occurs through airways maintained in substantially the same configuration during sleep as when awake, and snoring is eliminated. Equally important, obstructive sleep apnea is either drastically reduced or eliminated altogether.

Logical as the treatment taught by the invention might seem in retrospect, physicians and hosts of inventors have unsuccessfully sought an answer to the problem for centuries. The extraordinarily simple means of solving the problem—the use of muscle relaxants—has been available for decades, but no one has previously recognized it.

It is important to note that only those muscle relaxants that function at the spinal or supra-spinal level, i.e., above the neuro-muscular synapse, should be used in the treatment of snoring or obstructive sleep apnea. Muscle relaxants that act intrinsically in the muscle contraction per se or function as central nervous system depressants should be avoided because of their profound effect on the respiratory muscles, and consequently their potential jeopardizing of the respiratory function itself. Similarly, muscle relaxants known to be habit-forming should be avoided.

The presently preferred muscle relaxant for use in the treatment of snoring and obstructive sleep apnea is orphenadrine (2-dimethylaminoethyl 2-methylbenzhydryl ether) or its salts, e.g., orphenadrine citrate, commercially available from Riker Laboratories Inc. under the registered trademark "Norflex." Normally effective doses to date have ranged from 50 to 300 mg, taken orally before retiring; the required amount is somewhat dependent on the weight of the patient, but for most persons 100 mg proves satisfactory. Relief typically is obtained the first night, although for other persons, as much as a month may be required to completely eliminate the problem. At any rate, after relief is obtained, the dosage may be reduced to perhaps half of the initial amount. Persons afflicted with snoring may elect to remain permanently on the maintenance amount or, alternatively, to use the muscle relaxant only when snoring constitutes a social problem. If, of course, there is evidence of significant sleep apnea, the patient's health suggests that nightly dosing is desirable.

Other muscle relaxants believed to be effective in the practice of the invention include 4-amino-3(p-chlorophenyl butyric acid), commercially available from Geigy Pharmaceuticals under the registered trademark "Lioresal," quinine sulfate, commercially available from Merrell Dow Pharmaceuticals Inc. under the trade name "Quinamm," and 5-chloro benzoxazolinone, commercially available from McNeil Pharmaceutical under the registered trademark "Paraflex." It is possible that some muscle relaxants having sedating properties may also be effective if compounded with a stimulant such as an amphetamine or methylphenidate hydrochloride.

What is claimed is as follows:

1. A method of inhibiting or preventing snoring and associated obstructive sleep apnea comprising administering to a person displaying such symptoms an effective amount of orphenadrine citrate.

2. The method of claim 1 wherein the muscle relaxant is administered in an amount of about 50–300 mg prior to the patient's retiring.

3. A method of inhibiting or preventing snoring and associated abstructive sleep apnea comprising administering to a person displaying such symptoms an effective amount of muscle relaxant acting at the spinal or supra-spinal level and selected from the class consisting of orphenadrine, orphenadrine citrate, 4-amino-3(p-chlorophenyl butyric acid), quinine sulfate and 5-chloro benzoxazolinone.

* * * * *